United States Patent
Samadpour

(10) Patent No.: US 12,287,315 B2
(45) Date of Patent: Apr. 29, 2025

(54) RAPID RELIABLE DETECTION OF PATHOGENS IN FRESH FOODS

(71) Applicant: Institute for Environmental Health, Inc., Lake Forest Park, WA (US)

(72) Inventor: Mansour Samadpour, Lake Forest Park, WA (US)

(73) Assignee: Institute for Environmental Health, Inc., Lake Forest Park, WA (US)

( * ) Notice: Subject to any disclaimer, the term of this patent is extended or adjusted under 35 U.S.C. 154(b) by 640 days.

(21) Appl. No.: 17/605,823

(22) PCT Filed: Apr. 27, 2020

(86) PCT No.: PCT/US2020/030133
§ 371 (c)(1),
(2) Date: Oct. 22, 2021

(87) PCT Pub. No.: WO2020/220041
PCT Pub. Date: Oct. 29, 2020

(65) Prior Publication Data
US 2022/0205968 A1    Jun. 30, 2022

Related U.S. Application Data

(60) Provisional application No. 62/838,904, filed on Apr. 25, 2019.

(51) Int. Cl.
*G01N 33/02* (2006.01)
*C12Q 1/02* (2006.01)
*C12Q 1/04* (2006.01)

(52) U.S. Cl.
CPC .......... *G01N 33/02* (2013.01); *G01N 33/025* (2013.01); *C12Q 1/02* (2013.01); *C12Q 1/04* (2013.01)

(58) Field of Classification Search
CPC ...... G01N 33/02; G01N 33/025; G01N 33/04; G01N 33/12; C12Q 1/02; C12Q 1/04; Y10T 436/25; Y10T 436/25375; Y10T 436/255
USPC ........ 436/20–23, 174, 177, 178; 435/30, 34, 435/39
See application file for complete search history.

(56) References Cited

U.S. PATENT DOCUMENTS

| | | | |
|---|---|---|---|
| 5,843,699 A * | 12/1998 | Strenkoski | C12Q 1/04 435/308.1 |
| 2001/0008887 A1 * | 7/2001 | Choudary | G01N 33/56916 514/100 |
| 2004/0241644 A1 | 12/2004 | Samadpour | |
| 2017/0369924 A1 * | 12/2017 | Pilarski | C12Q 1/6806 |
| 2018/0258458 A1 * | 9/2018 | Sitton | C12Q 1/10 |

OTHER PUBLICATIONS

FDA.gov "BAM: *Salmonella*," Dec. 2007, <https://www.fda.gov/media/83330/download> [retrieved Jun. 17, 2020], p. 7, paragraph 15.

King, N., and Dr. A. Hudson, "Detection and Enumeration of Yersinia Enterocolitica from Raw Pork: Plot Survey," Institute of Environmental Science & Research Limited, Jun. 2006, <https://www.mpi.govt.nz/dmsdocument/25982/direct> [retrieved Jun. 17, 2020], p. 8.

Suslow, T., "Validation of Rapid Pathogen Detection Methods and Kits Applied to Pre-Harvest Operations for Leafy Greens Production," 2011. <http://calgreens.org/control/uploads/Food_Safety_-_Pathogen_Detection_Kits1.pdf> [retrieved Jun. 17, 2021], pp. 3-5 and Table 1.

International Search Report and Written Opinion mailed Jul. 17, 2020, in International Patent Application No. PCT/US2020/030133, filed Apr. 27, 2020, 14 pages.

* cited by examiner

*Primary Examiner* — Maureen Wallenhorst
(74) *Attorney, Agent, or Firm* — Barry L. Davison; Davis Wright Tremaine LLP

(57) ABSTRACT

Provided are methods for rapid detection of microbial contaminants in fresh foods, involving obtaining a product sample (preferably at or near the time of harvest of the product), applying, prior to any chilling of the sample or the product, an amount of a enrichment medium sufficient to cover the sample surfaces to provide a non-chilled sample for incubation, incubating the non-chilled sample for a time period and at a temperature sufficient to allow for amplification and enrichment of a non-cold-shocked target microbe, followed by recovering all or a portion of the enrichment media, concentrating the target microbes from the recovered enrichment medium, and detecting the concentrated target microbes.

12 Claims, No Drawings

RAPID RELIABLE DETECTION OF PATHOGENS IN FRESH FOODS

CROSS-REFERENCE TO RELATED APPLICATIONS

This application is a 371 National Phase Application of International Patent Application No. PCT/US2020/030133, filed Apr. 27, 2020, which claims the benefit of U.S. Provisional Patent Application No. 62/838,904, filed Apr. 25, 2019, the disclosures of which are incorporated herein by reference in their entirety.

FIELD OF THE INVENTION

Certain aspects relate to methods for rapid detection of microbial contaminants (e.g., in fresh foods), and in more particular aspects to methods that avoid cold-shock, and comprise dilution minimizing enrichment, and subsequent concentration of microbial targets prior to detection.

BACKGROUND OF THE INVENTION

It is commonly accepted that reliable detection of bacterial and fungal pathogens in, for example, foods, pharmaceuticals, nutraceuticals and environmental samples requires enrichment to detection level. This requirement is based on the premise that where low levels of target microbes/pathogens are to be detected in a sample, reliance on concentration steps, such as magnetic beads, etc., can fail due to the chemistry of the enrichment/enrichment medium and/or the presence of auto-agglutinating bacteria. Moreover, it is generally accepted that there is no extraction step that can ensure recovery of 100% of the target organisms when the targets are there in extremely low numbers.

While it may be possible to reliably detect pathogens present at low levels by using 8-12 hours of enrichment incubation/range, there are instances that even this short of a period is not practical for fresh food producers. For example, in the produce industry there are producers that, for practical, economic reasons, would like to use a total of only 6-7 hours between the harvest and the processing of the harvested materials, followed by immediate shipping of the processed materials. Likewise, in the meat industry there is a practical need to detect pathogens on carcasses or in the trim and other products in less than 8 hours.

However, if current assay methods used such desired shorter enrichment incubation periods, which are shorter than currently accepted periods for achieving detectable microbe levels, such assays would not be reliable, and would not provide for regulatory compliance.

SUMMARY OF PARTICULAR ASPECTS OF THE INVENTION

Embodiments of the disclosure can be described in view of the following clauses:

1. A method for rapid detection of microbial contaminants in one or more product samples, comprising: obtaining a sample of a product prior to any chilling of the sample or the product; applying an amount of a enrichment medium sufficient to cover the sample surfaces to provide a non-chilled sample for incubation; incubating (e.g., immediately) the non-chilled sample for a time period, and at a temperature sufficient to allow for amplification and enrichment of a non-cold-shocked target microbe potentially present in the non-chilled sample to provide an enriched sample; recovering all or a portion of the enrichment media from the enriched sample; concentrating the target microbes from the recovered enrichment medium to provide recovered concentrated target microbes; and detecting the target microbes, using at least the portion of the recovered concentrated target organisms.

2. The method of clause 1, wherein the enrichment medium, prior to applying, is pre-adjusted to the sufficient incubation temperature.

3. The method of clause 1 or clause 2, wherein the enrichment medium contains a surfactant and/or a wetting agent present in sufficient concentration to insure providing a coating or film on all the sample surfaces.

4. The method of clause 3, wherein the coating or film provides at least a micro layer (e.g., between 1 µm and 1 mm) of the enrichment medium on all of the sample surfaces.

5. The method of any one of clauses 1-4, wherein the sample is collected at or near a time of harvest of the product.

6. The method of any one of clauses 1-5, wherein applying the enrichment medium is to a composited sample.

7. The method of any one of clauses 1-6, wherein the amount of the enrichment medium sufficient to cover the sample surfaces provides for microbial growth while minimizing dilution of microbes.

8. The method of any one of clauses 1-7, wherein incubating at the sufficient temperature comprises incubating at one or more temperatures in a range of 32° C. to 45° C.

9. The method of any one of clauses 1-8, wherein incubating at the sufficient temperature comprises incubating using a transport incubator, preferably at one or more temperatures in a range of 32° C. to 45° C.

10. The method of any one of clauses 1-9, wherein incubating at the sufficient temperature is for a period of time of about 2 to about 6 hrs, about 2 to about 5 hrs, about 2 to about 4 hrs, about 3 to about 6 hrs, about 3 to about 5 hrs, or preferably about 3 to about 4 hrs.

11. The method of any one of clauses 1-10, wherein concentrating the target microbes from the recovered enrichment medium comprises one or more of centrifugation, and/or filtration, and/or immunomagnetic beads, and/or affinity-magnetic beads.

12. The method of any one of clauses 1-11, wherein providing recovered concentrated target microbes comprises suspending the recovered concentrated target microbes in a minimal volume of a buffered solution, to provide a 100-fold to 1000-fold concentration of the target microbe relative to the recovered enrichment medium.

13. The method of any one of clauses 1-12, wherein detecting the target microbes comprises use of one or more of a nucleic acid-based assay, and/or immunochemical based-based assay, and/or target amplification based-assay, and/or bacteriophage-based detection assay.

DETAILED DESCRIPTION OF THE INVENTION

According to aspects of the present invention, it is possible to expedite microbial detection for fresh food producers, e.g., for fresh foods like fresh produce, fruits and vegetables at the time of harvest, fresh meats after slaughter and before chilling, fresh seafood at harvest before cooling, fresh sprouts before washing and cooling, fresh dairy products before refrigeration, fresh bakery products before freezing, and any kind of foods in which target microbes are at a growing range of temperature.

In the methods, sample portions may be taken (e.g., a sample or a composited sample formed), prior to cold shock of the product (e.g., product lot). In the case of fresh produce, vegetables, fruits and the like, samples may be taken, e.g., at the farm, or greenhouses before chilling/cooling. For meats at slaughter, samples may be taken, e.g., before the hot box or at the hot box, before the carcasses are chilled. For milk, samples may be taken, e.g., at the milking parlor before refrigeration. In such manner, cold-shock of the product, and of any microbes present thereon, is avoided, which is contrary to the normal practice of the industry which is to place samples in coolers and refrigerators as quickly as possible to maintain freshness and suppress microbial growth.

In the methods, by avoiding cold-shock, the lag phase during the enrichment incubation period may be reduced or eliminated, and this alone can expedite the timeline to achieve detection results by 60-90 minutes.

In the methods, enrichment incubation may, and preferably should be commenced as close as possible to harvest of the product. This may be achieved, for example, by using transport incubators and pre-warmed media, to facilitate starting the sample enrichment as close to the harvest as possible to save additional time. For example, covering (e.g., with a volume, coating or film) the sample with pre-warmed media may be used in combination with transport incubators (e.g., having temperature ranges of 32° C.-45° C.), thus allowing the sample to enrich immediately for a relatively short period of time (e.g., 3-4 hours) to allow for amplification of the target organism(s).

In the methods, samples may be, and preferably are enriched using a minimal amount of media, sufficient to cover or coat the sample or sample portions (e.g., of a composite lot sample). The media may, for example, contain an appropriate amount of surfactants/wetting agent(s) to ensure that the medium/media cover the surfaces of the sample (e.g., with at least a micro layer (e.g., between 1 μm and 1 mm) of the enrichment media). This micro-enrichment protocol allows for target microbes (e.g., pathogens) to grow in the context of a coating/film, while minimizing or preventing dilution of the target microbes.

In the methods, all or a portion of the incubated, enrichment medium from the enriched coated sample may be recovered, followed by concentrating of the target microbes (e.g., using a concentration step including, for example, centrifugation and/or filtration and/or use of immunomagnetic beads and/or affinity-magnetic beads and/or any suitable concentration method or affinity concentration process. Preferably, in the methods, concentration may be sufficient to provide at least a 100-fold to 1000-fold concentration of the target microbe(s) relative to the recovered enrichment medium prior to such processing/concentration. The recovered microbial concentrate may, for example, be re-suspended in minimal volumes of a buffer (e.g., to provide buffered solution containing concentrated microbes), to achieve e.g., at least a 100-fold to 1000-fold concentration of the target microbe(s) relative to the recovered enrichment medium prior to such processing/concentration.

In the methods, the recovered, concentrated microbes may then subjected to a rapid detection assay/module to detect one or more target microbes (e.g., pathogens). For example, a portion of the recovered, concentrated cells may be tested using, e.g., nucleic acid-based detection assay(s), and/or immunochemical-based detection assay(s), and/or target amplification-based detection assay(s), and/or bacteriophage-based detection assays, and/or any other suitable detection assay.

The methods are surprisingly effective, and are contraindicated by the pervasive industry practice of placing samples in coolers and refrigerators as quickly as possible (prior to sampling and enrichment culturing) to maintain freshness and suppress microbial growth. Likewise, it is commonly accepted that reliable detection of bacterial and fungal pathogens (e.g., in foods, pharmaceuticals, nutraceuticals and environmental samples, etc.) requires enrichment to detection levels, based on the premise that where low levels of target microbes/pathogens are to be detected, reliance on concentration steps (e.g., centrifugation, and/or filtration, and/or immunomagnetic beads, and/or affinity-magnetic beads, etc.), can fail due to the chemistry of the enrichment/enrichment medium and/or the presence of auto-agglutinating bacteria. Moreover, it is generally accepted that there is no extraction step that can ensure recovery of 100% of the target organisms when the targets are there in extremely low numbers.

The invention claimed is:

1. A method for rapid detection of microbial contaminants in one or more product samples, comprising:
    obtaining a sample of fresh produce, fruits, or vegetables at or near a time of harvest, and prior to any chilling of the sample;
    applying only an amount of enrichment medium to the sample which is sufficient to provide a micro layer of between 1 μm and 1 mm of enrichment medium on all surfaces of the sample to provide a non-chilled coated sample for incubation;
    incubating the non-chilled coated sample for a time period, and at a temperature sufficient to allow for amplification and enrichment of a non-cold-shocked target microbe potentially present in the non-chilled sample to provide an enriched sample;
    recovering all or a portion of the enrichment medium from the enriched sample;
    concentrating the target microbe from the recovered enrichment medium to provide recovered concentrated target microbes; and
    detecting the recovered concentrated target microbes.

2. The method of claim 1, wherein the enrichment medium, prior to applying, is pre-adjusted to the sufficient incubation temperature.

3. The method of claim 1, wherein the enrichment medium contains a surfactant and/or a wetting agent.

4. The method of claim 1, wherein the sample is collected at the time of harvest of the fresh produce, fruits, or vegetables.

5. The method of claim 1, wherein applying the enrichment medium is to a composited sample.

6. The method of claim 1, wherein the amount of the enrichment medium is sufficient to provides for microbial growth while minimizing dilution of microbes.

7. The method of claim 1, wherein incubating at the sufficient temperature comprises incubating at one or more temperatures in a range of 32° C. to 45° C.

8. The method of claim 1, wherein incubating at the sufficient temperature comprises incubating using a transport incubator at one or more temperatures in a range of 32° C. to 45° C.

9. The method of claim 1, wherein incubating at the sufficient temperature is for a period of time of about 2 to about 6 hrs, about 2 to about 5 hrs, about 2 to about 4 hrs, about 3 to about 6 hrs, about 3 to about 5 hrs, or about 3 to about 4 hrs.

10. The method of claim 1, wherein concentrating the target microbes from the recovered enrichment medium comprises one or more of centrifugation, and/or filtration, and/or immunomagnetic beads, and/or affinity-magnetic beads.

11. The method of claim 1, wherein providing recovered concentrated target microbes comprises suspending the recovered concentrated target microbes in a minimal volume of a buffered solution, to provide a 100-fold to 1000-fold concentration of the target microbes relative to the recovered enrichment medium.

12. The method of claim 1, wherein detecting the recovered concentrated target microbes comprises use of one or more of a nucleic acid-based assay, and/or immunochemical-based assay, and/or target amplification-based assay, and/or bacteriophage-based detection assay.

* * * * *